(12) United States Patent
Meier et al.

(10) Patent No.: US 7,477,724 B2
(45) Date of Patent: Jan. 13, 2009

(54) X-RAY INSTRUMENT

(75) Inventors: Roger Meier, Almelo (NL); Sebastian Gehrke, Erlangen (DE); Karl-Ernst Wirth, Erlangen (DE)

(73) Assignee: PANalytical B.V., Almelo (NL)

( * ) Notice: Subject to any disclaimer, the term of this patent is extended or adjusted under 35 U.S.C. 154(b) by 198 days.

(21) Appl. No.: 11/377,908

(22) Filed: Mar. 16, 2006

(65) Prior Publication Data

US 2006/0215818 A1  Sep. 28, 2006

(30) Foreign Application Priority Data

Mar. 17, 2005  (EP)  .................................. 05251611

(51) Int. Cl.
*G01N 23/223* (2006.01)
(52) U.S. Cl. .............................. 378/45; 378/70; 378/80
(58) Field of Classification Search ............. 378/44–47, 378/70–90
See application file for complete search history.

(56) References Cited

U.S. PATENT DOCUMENTS

| | | | |
|---|---|---|---|
| 3,469,095 A * | 9/1969 | Starnes ........................ 378/46 |
| 3,655,964 A | 4/1972 | Slight .................... 250/43.5 D |
| 3,925,661 A | 12/1975 | Carr-Brion .................. 250/272 |
| 4,090,073 A | 5/1978 | De Villiers et al. .......... 250/273 |
| 4,180,735 A | 12/1979 | Sipila et al. ............. 250/358 R |
| 4,582,992 A | 4/1986 | Atwell et al. ............ 250/359.1 |

OTHER PUBLICATIONS

International Search Report dated Dec. 5, 2005.
Grassler et al., "X-ray Computer Tomography—Potential and Limitation for the Measurement of Local Solids Distribution in Circulating Fluidized Beds," *Chemical Engineering Journal*, vol. 77:65-72, 2000.

* cited by examiner

*Primary Examiner*—Jurie Yun
(74) *Attorney, Agent, or Firm*—Bromberg & Sunstein LLP

(57) ABSTRACT

X-ray apparatus 10 includes an X-ray source (22), an X-ray detector (28) facing the X-ray source. Inlet (6) accepts a stream of particles and a guide system (18) guides the stream of particles (16) in free space between the X-ray source (22) and detector (28) so that X-ray analysis can be carried out on the particles in the stream (16) in a sample region (21) between the source (22) and the detector (28).

19 Claims, 4 Drawing Sheets

X-RAY INSTRUMENT

CROSS REFERENCE TO RELATED APPLICATIONS

This application claims priority from European Patent Application Serial No. 05251611.9, filed on Mar. 17, 2005, which is hereby incorporated by reference, in its entirety.

TECHNICAL FIELD

The invention relates to an X-ray instrument, which may be for example an X-ray Fluorescence (XRF) apparatus or an X-ray Diffractometer (XRD), and in particular to XRD or XRF apparatus for measuring particles or powders.

BACKGROUND ART

X-ray diffraction is a well known technique for measuring the physical properties of materials. The diffraction of X-rays gives a measure of the spacing between planes of atoms, and the measured intensities and spacings of the peaks can be used to calculate the proportions of various crystalline phases in a sample.

X-ray fluorescence is another well known technique in which X-rays are used to determine the relative amounts of atoms using their characteristic fluorescence spectra.

Such techniques can be used to measure the chemical and phase composition of samples during or after manufacturing. Increasingly, analysis is carried out during manufacture rather than simply being used to test the finished product. By doing this, it is possible to adjust the manufacturing process to improve the final result rather than simply needing to reject samples that fail quality control standards.

For example, in the cement industry, it can be desirable to test the cement during manufacture for a number of different additives, including sulphates and carbonates. Normally, such testing is carried out after manufacture, that is to say, off-line. However, the inventors are aware of one approach in which a continuous stream of cement is analysed, using equipment developed by the CSIRO of Australia and marketed by FCT- ACTech. Another approach using X-rays is X-ray computer tomography, for example as set out in "X-ray computer tomography—potential and limitation for the measurement of local solids distribution circulating fluidized beds", Grassler and Wirth, Chemical Enginerering Journal 77 (1-2) (2000) pages 65 to 72.

However, there remains a need for improved X-ray apparatus for carrying out X-ray studies of particle or powder material.

SUMMARY OF INVENTION

According to the invention there is provided an X-ray apparatus comprising:
  an X-ray source;
  an X-ray detector facing the X-ray source for detecting X-rays travelling along an X-ray path from source to detector;
  an inlet for accepting a stream of particles;
  a guide system arranged to guide the stream of particles between the X-ray source and detector so that X-ray analysis can be carried out on the particles in the stream in an analysis region between source and detector, the stream of particles being spaced from solid parts of the X-ray apparatus in the analysis region.

By providing the stream of particles spaced from solid parts of the apparatus analysis of the particles can be carried out without interference from sidewalls. The particles are not in contact with the apparatus in the analysis region.

Note that the requirement for the stream of particles to be spaced from solid parts of the apparatus does not mean that there can be no walls, windows or solid material between the source and detector. However, it is much easier to distinguish X-rays from such walls, windows or solid material spaced apart from the stream of particles than it is to distinguish X-rays from walls or windows in contact with the sample stream of particles from X-rays from the stream of particles itself.

Further, if windows, guide plates, or conveyors were to be used to contain the stream of particles the windows may be abraded very quickly. It will be appreciated that along the X-ray path the materials used need to be transparent to X-rays which significantly reduces the choice and thickness of materials used.

The invention uses a transmission geometry in which the sample region is between the source and detector and in which X-rays are generated and pass through the sample stream allowing X-rays to be measured. By using the transmission geometry it is possible to sample the complete thickness of the sample stream. A reflection geometry would only measure the top of the dense sample stream, to a penetration depth which will depend on the specific material but which may be 0.2mm to 0.3mm, reducing the signal measured by the detector.

Further, since no sample preparation is required, the sample is not affected by the sample preparation. For example, Gypsum is dehydrated by pressing which changes the sample.

Moreover, the particles of the sample stream are not generally perfect spheres so the provision of any walls, beds or indeed any physical constraint for the sample stream would in general cause the particles of the sample stream to have a preferred orientation. In general, it is desirable for the particles to be randomly oriented and this is achieved using the invention by having the sample stream in free space, the particles therefore being free to rotate.

The invention is of particular application in areas such as cement manufacture where streams of particles can conveniently be measured on-line as part of the manufacturing process. Prior approaches in this industry have taken cement powder and formed compacted powder discs which have been introduced into conventional X-ray diffraction approach. However, such discs do not have the particles randomly oriented and this reduces the reliability of the diffraction or fluorescence results. In contrast, the invention provides free particle streams which are essentially unoriented, thereby improving results.

The guide system may include an entrainment gas inlet for creating a gas stream between the source and detector and a mixing chamber for mixing the stream of particles with the gas stream.

The guide system may be arranged to provide a stream of particles entrained in a fluid with a density of between 1% and 70% of the density of the particles. In the invention, a high particle density is highly desirable to improve the results. In contrast, in other applications that might need to measure particle streams, for example to measure particle size by laser light, much lower densities would be appropriate.

The guide system may comprise a nozzle connected to the inlet to direct the stream of particles in free space between the source and detector.

There are a number of ways to guide the stream through the sample region.

In one approach, the guide system includes a pair of opposed electrostatic plates on either side of the sample nozzle for charging with a first polarity and a receiving electrostatic plate on the other side of the sample region for charging with a second polarity opposite to the first polarity. This creates a converging electrostatic field to guide the stream through the sample region.

In an alternative approach, the guide system comprises a sample nozzle shaped to output the stream of particles and opposed gas nozzles on either side of the nozzle to direct gas on either side of the stream in parallel with the stream to guide the stream of particles through the sample region.

In either case, the nozzle may be shaped to have a flat inner cavity and a slit exit the outside of the nozzle tapering at the exit to direct the stream of particles between the source and detector. Experiment has shown this form of nozzle can give good results.

The nozzle may be shaped to generate a stream of particles in the form of a flat sheet having a thickness of less than 2 mm and a width of at least 5 mm preferably 15 mm. This is convenient for X-ray measurements.

The X-ray apparatus may include protective plates between the sample region and the source and between the sample region and the detector, the protective plates being transparent to X-rays and spaced from the sample region so that the plates are spaced from the stream of particles in use. This can reduce damage to the apparatus.

In another aspect the invention relates to a method of operation of an X-ray apparatus, comprising: guiding a stream of particles in free space through a sample region and transmitting X-rays from a source through the sample region to a detector to measure the properties of the stream of particles.

BRIEF DESCRIPTION OF DRAWINGS

For a better understanding of the invention, an embodiment will now be described, purely by way of example, with reference to the accompanying drawings, in which.

Like components are given the same reference numerals in different figures and the description of the components is not repeated with respect to each figure.

DETAILED DESCRIPTION

Figure 1:
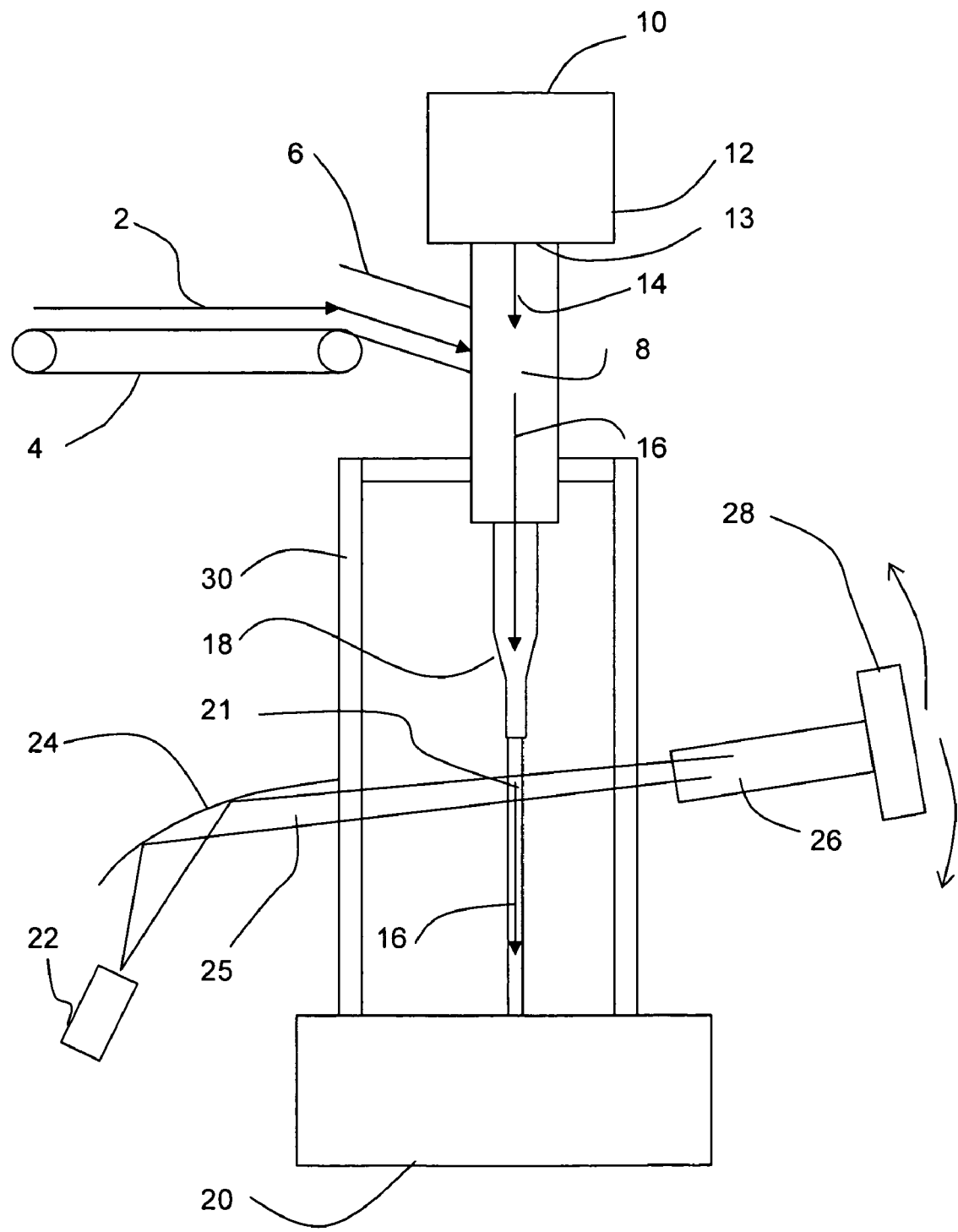
FIG. 1 shows an embodiment of an X-ray diffraction apparatus according to the invention.

Referring to FIG. 1, an X-ray diffraction apparatus is shown. A stream of powder 2 is carried towards the X-ray apparatus 10, as shown schematically by conveyor 4, and introduced into hopper or cell wheel 6.

The X-ray apparatus 10 includes a pump 12 which creates a flow, in the example of air 14 flowing downwards through inlet 13. Then, the stream of powder 2 is introduced into the stream of air 14 in mixing chamber 8 to form what is, in the embodiment, a sample stream 16 of powder entrained in the downward flowing air.

The sample stream 16 is then passed out through nozzle 18 where it flows freely until it arrives at collection hopper 20.

The X-ray apparatus also includes an X-ray source 22 and an X-ray mirror 24 for directing an X-ray beam along X-ray path 25 emitted by the X-ray source 12 through the sample stream 16 in sample region 21. An monocromator 26 and an X-ray detector 28 is arranged to detect the X-rays, and may be rotated as indicated by the arrows.

Shields 30 that are transparent to X-rays are provided to protect the source 22, mirror 24, analyser crystal 26 and detector 28 from the sample stream. Note that the shields 30 are well spaced from the sample stream 16 along the X-ray path 25. This has the effect that it is easy to distinguish X-rays from the shields 30 from X-rays emitted by the detector 28.

In use, the detector 26 is rotated to carry out a scan of the material in the continuous sample stream 16.

Note that whereas conventional X-ray diffraction apparatus often uses a reflection approach the invention uses a transmission approach. The mirror 24 may conveniently be an elliptical, focussing mirror to provide a converging beam.

The sample stream 16 should not just be a few widely spaced particles in the air stream 14 which would not normally provide a sufficiently strong but sufficiently dense to provide a good diffraction pattern. Typically, the sample stream 16 should have a density in the range 1% to 70% of the density of the solid from which the sample stream 16 is made up of. The density should not however be so dense to prevent the particles freely moving and the absorbtion/interaction should be in the order of between 20 and 80%)

This dense, loose, sample stream of flying particles provides a good rotation of the particles as they fly in the stream and avoids there being a preferred orientation. This delivers good averaging and so the quality of data that may be obtained from the invention is generally better than that obtained in prior art approaches.

Figure 2:
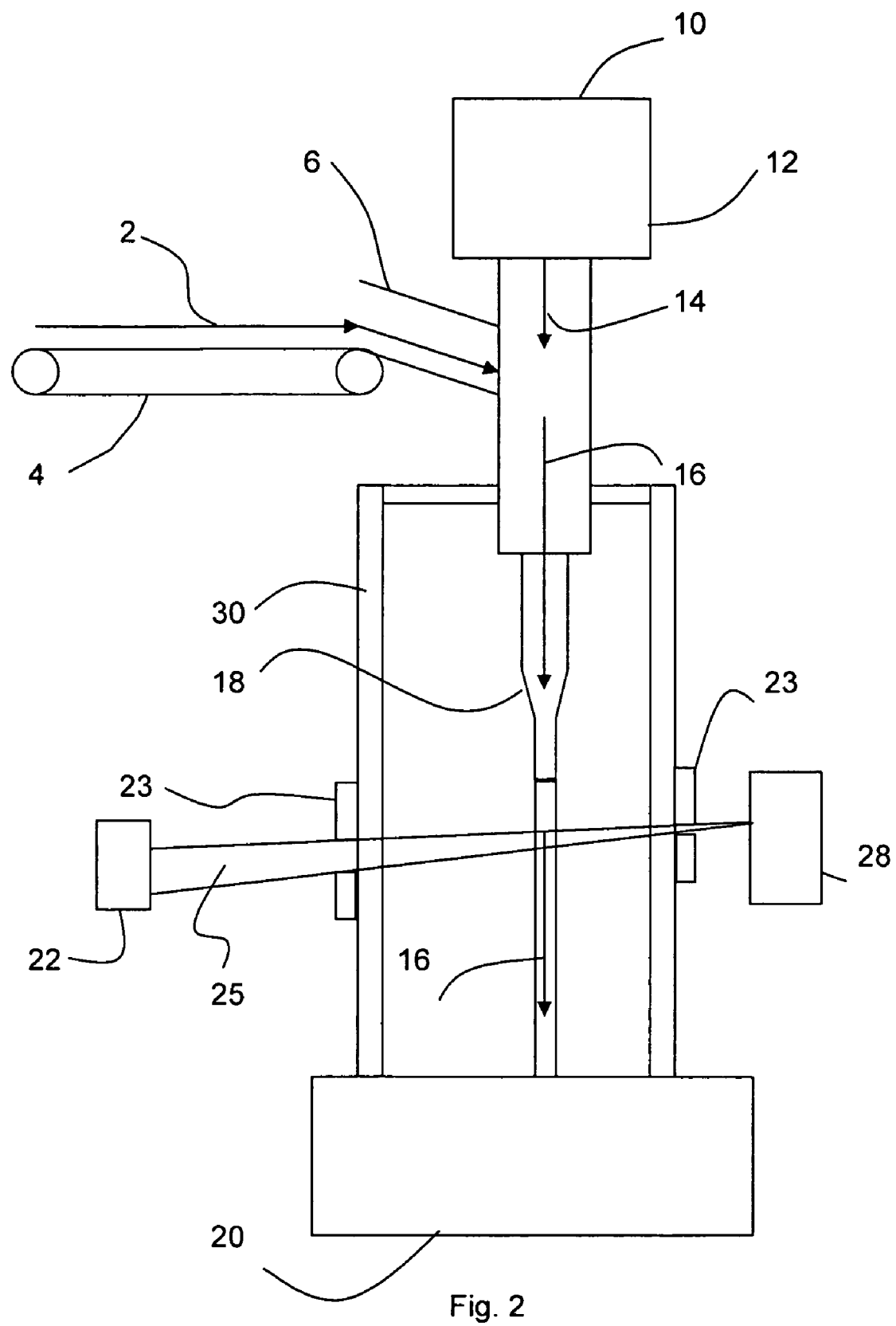
FIG. 2 shows an embodiment of an X-ray fluorescence apparatus according to the invention.

It will be appreciated that the invention is equally applicable to X-ray fluorescence measurements and FIG. 2 illustrates a suitable X-ray fluorescence apparatus according to an embodiment of the invention, which is very similar to that of FIG. 1 except that the mirror 24 and detector 26 is omitted and collimators 23 added.

The skilled person will realise that getting the sample stream 16 with particles to flow through free space for a significant distance requires some care. There are two steps, firstly the mixing of the air stream 14 and particle stream 2 to arrive at the sample stream 16, and secondly the projection of this stream through the sample region 21.

The inventors have found that it is beneficial to provide a continuous smoothly flowing air stream 14 and to add the particle or powder stream 2 to the air stream 14. As shown in FIG. 1, the air stream 14 and sample stream 16 may move in the same direction, with the particle stream 2 added from the side.

It is also possible to use relatively complex approaches for mixing the streams, such as that using a riser as set out in the aforementioned paper by Grassier and Wirth.

The approach used to eject the sample stream 16 is also important.

Figure 3:
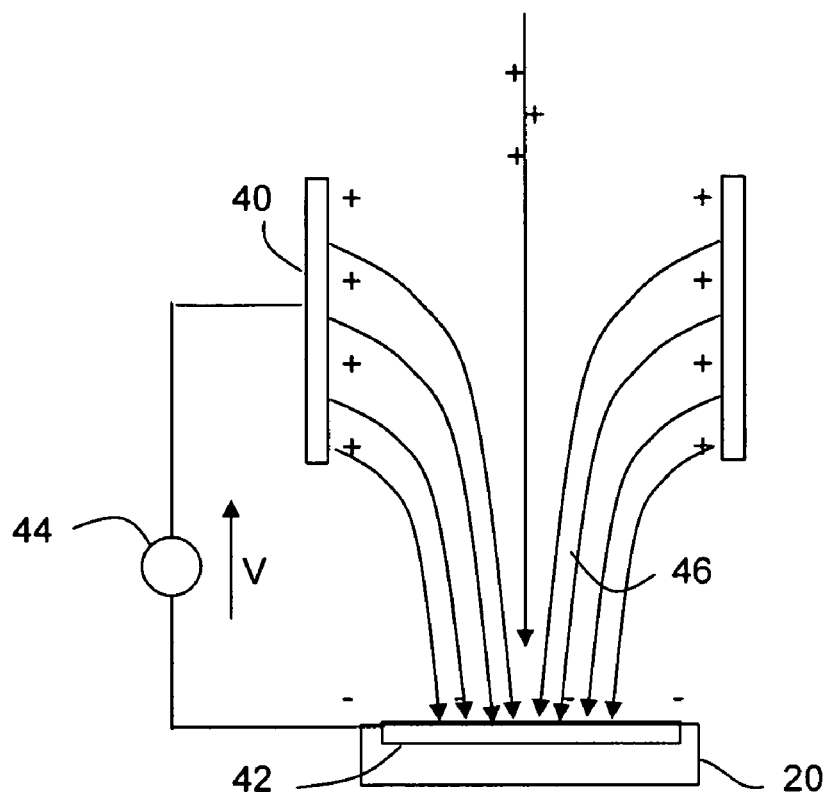
FIG. 3 illustrates an electrostatic guidance system used in an embodiment of the invention.

One approach, as illustrated in FIG. 3, is to electrostatically charge the particles of the sample stream 16, and to use a pair of opposed guide plates 40 on either side of the stream and a base guide plate 42 at the collection hopper 20. The base guide plate 12 may be, for example, a grid. Assuming that the particles are electrostatically charged to be positive, the opposed guide plates 40 may be positive and the base guide plate 42 negative leading to a converging electric field 46 as shown in FIG. 3 which tends to keep the flowing sample stream 16 together. The electric power supply 44 indicated in FIG. 3 maintains the electrostatic charge.

Figure 4:
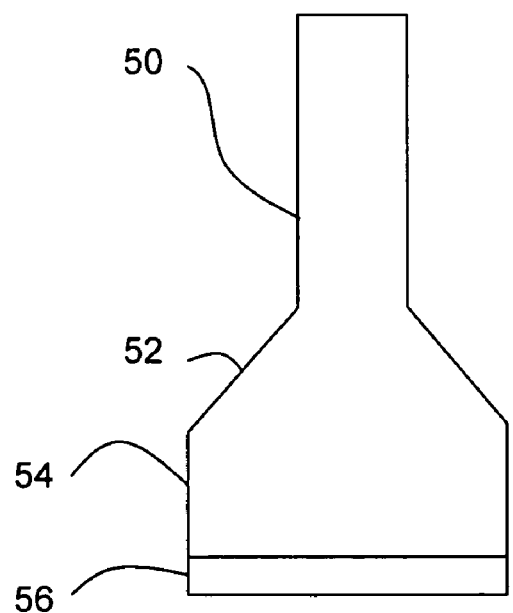
FIG. 4 is a top view of a nozzle used in an embodiment of the invention.
Figure 5:
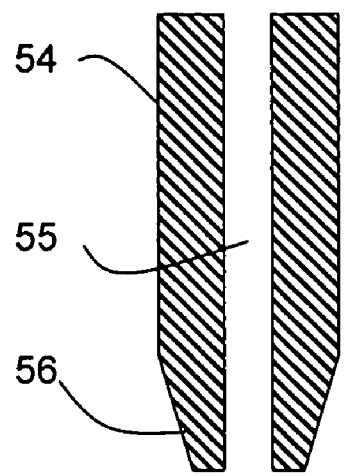
FIG. 5 is a side view of a nozzle used in an embodiment of the invention.

The nozzle 18 may be carefully shaped as illustrated in FIG. 4 (front view) and FIG. 5 (side section). Note in this case that the nozzle 18 includes a feed part 50, an expanding part 52, and a delivery part 54. At the end of the delivery part 54, there is an ejection part 56 which forms the ejection end of the delivery part 54. The expanding part 52 viewed from the front provides an expanded stream and the delivery part 54 viewed from the front has substantially straight sides. Viewed from the side, the walls in the ejection part 56 taper so that the inside defines an inner cavity 55 having constant cross section but in which the outside of the ejection part 56 tapers.

The outer thickness of the main portion of the delivery part is 3 mm, falling to 2.4 mm at the end of the ejection part, with nozzles of 0.8 mm thickness. The thickness of the interior of the nozzle is 0.8 mm throughout the delivery part 54. Thus, the nozzle 18 is effectively in the shape of a slit having a constant cross section (thickness) in the ejection part 56, being much wider than it is thick, and producing therefore a ribbon-shaped particle sample stream 16.

In the specific embodiment shown, the delivery part 54 has a length of 30 mm and the expanding part 52 has a length of 25 mm. The feed part 50 is a tube of inner diameter 4 mm. The width of the wide delivery part is 26 mm.

Those skilled in the art will realise that these dimensions are not essential and other systems may require different dimensions.

The ejection part 56 is thus in the form of a slit of width 26 mm and thickness 0.8 mm.

Figure 6:
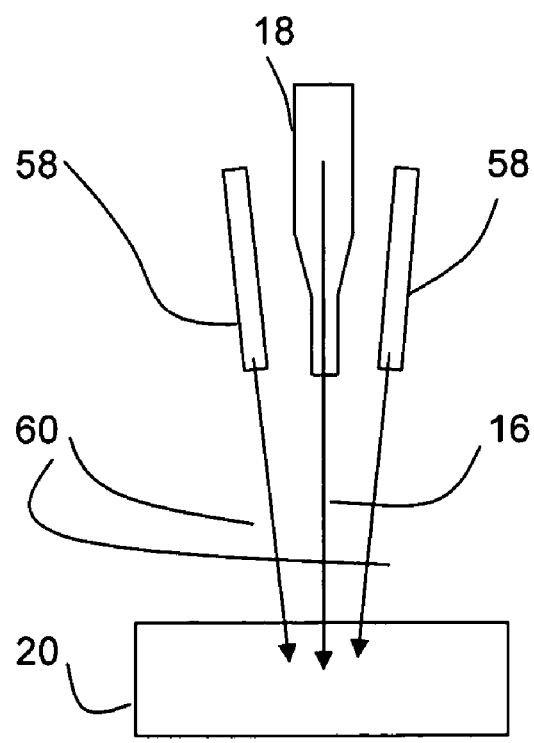
FIG. 6 shows guide streams used in an embodiment of the invention.

Alternatively or additionally to the electrostatic plates of FIG. 2, a further development is to provide additional air streams, as illustrated in FIG. 6, which shows nozzle 18 as above and two guide nozzles 58, one on each side of the nozzle 18, spaced from nozzle 18 in the thickness direction. The guide nozzles emit guide air streams 60, in the form of sheets of air on either side of the sample stream 16, to guide the sample stream into collection hopper 20. It will be appreciated that this arrangement can be incorporated into the apparatus of FIG. 1 or FIG. 2.

In a particular embodiment, the guide nozzles 58 are combine with a nozzle 18 using the nozzle shape of FIGS. 4 and 5 in the arrangement of FIG. 6, without using electrostatic plates.

In use, the embodiments allow the measurement of those properties that may be determined by X-rays. For example, in the cement industry, X-ray diffraction may be used to determine the quantity of different sulphates and carbonates in the cement, which are an important parameters. The invention allows accurate real time measurements to be made of a sample stream.

An alternative application area is in the pharmaceutical industry where an accurate measurement of the composition of powders used to make preparations of drugs is very useful.

The invention will is not limited to the embodiments and applications set out above.

Those skilled in the art will realise that there are many other applications where the invention might be useful, for example in the field of minerals and fine chemicals.

The exact shape of the nozzle and the guiding arrangements may be changed if required.

Although the above description describes the use of air to entrain the particles of the sample stream, other gas or liquid media such as nitrogen, solvents or inert gases can also be used to entrain and guide the sample stream.

The sample stream may be of any suitable material for X-ray analysis.

Although various exemplary embodiment of the invention have been disclosed, it should be apparent to those skilled in the art that various changes and modifications can be made which will achieve some of the advantages of the invention without departing from the true scope of the invention. These and other obvious modifications are intended to be covered by the claims that follow.

What is claimed is:

1. An X-ray apparatus comprising:
   an X-ray source;
   an X-ray detector facing the X-ray source for detecting X-rays;
   a particle inlet for accepting a stream of particles;
   a guide system arranged to guide the stream of particles between the X-ray source and detector so that X-ray analysis can be carried out on the particles in the stream in an analysis region, between source and detector, the stream of particles being spaced from solid parts of the X-ray apparatus in the analysis region;
   wherein the guide system comprises an entrainment gas inlet for creating a gas stream and a mixing chamber for mixing the stream of particles with the gas stream to produce a gas sample stream that delivers the particles in the gas sample stream through the analysis region.

2. An X-ray apparatus according to claim 1 wherein the gas sample stream has a density of between 100% and 70% of the density of the individual particles.

3. An X-ray apparatus according to claim 1 wherein the guide system comprises a sample nozzle connected to the particle inlet to direct the gas sample stream between the source and detector.

4. An X-ray apparatus according to claim 3 wherein the guide system includes a pair of opposed electrostatic plates on either side of the sample nozzle for charging with a first polarity and a receiving electrostatic plate on the other side of the analysis region for charging with a second polarity opposite to the first polarity to create a converging electrostatic field to guide the gas fluid sample stream through the analysis region.

5. An X-ray apparatus according to claim 3 wherein the sample nozzle is shaped to have a flat inner cavity and a slit exit, the width of the slit exit being narrower than the flat inner cavity, the outside of the sample nozzle tapering at the exit to direct the gas fluid sample stream between the source and detector.

6. An X-ray apparatus according to claim 3 wherein the sample nozzle is shaped to generate the gas sample stream in the form of a flat sheet having a thickness of less than 2 mm and a width of at least 5 mm.

7. X-ray apparatus according to claim 3 wherein the sample nozzle is shaped to output the gas sample stream and opposed gas nozzles are provided on either side of the sample nozzle to direct gas on either side of the gas sample stream in parallel with the gas sample stream to guide the gas sample stream through the analysis region.

8. An X-ray apparatus according to claim 1 further comprising protective plates between the analysis region and the source and between the analysis region and the detector, the protective plates being transparent to X-rays and spaced from the analysis region so that the plates are spaced from the gas sample stream in use.

9. X-ray apparatus according to claim 1 wherein the X-ray source is on one side of the analysis region arranged to transmit X-rays through the analysis region to the detector for carrying out X-ray analysis as a transmission arrangement.

10. X-ray apparatus according claim 9 further comprising an X-ray mirror between the X-ray source and the detector for focusing the X-rays through the analysis region towards the detector.

11. A method of operation of an X-ray apparatus, comprising:
   guiding a stream of particles in through an analysis region; and
   transmitting X-rays from a source through the analysis region along an X-ray path to a detector to measure the properties of the stream of particles in the analysis region spaced from solid parts of the X-ray apparatus along the X-ray path;
   wherein the step of guiding the stream of particles includes creating a gas fluid sample stream by mixing the stream of particles with a gas fl-ttiA stream in a mixing chamber and delivering the gas fl-tti-d sample stream to the analysis region.

12. An X-ray apparatus comprising:
   an X-ray source;
   an X-ray detector facing the X-ray source for detecting X-rays;
   a particle inlet for accepting a stream of particles;
   a guide system arranged to guide the stream of particles between the X-ray source and detector so that X-ray analysis can be carried out on the particles in the stream in an analysis region, between source and detector, the stream of particles being spaced from solid parts of the X-ray apparatus in the analysis region;
   wherein the guide system comprises an entrainment fluid inlet for creating a fluid stream and a mixing chamber for mixing the stream of particles with the fluid stream to produce a fluid sample stream that delivers the particles in the fluid sample stream through the analysis region, the guide system including a sample nozzle connected to the particle inlet to direct the fluid sample stream between the source and detector, the sample nozzle shaped to output the fluid sample stream and opposed gas nozzles are provided on either side of the sample nozzle to direct gas on either side of the fluid sample stream in parallel with the fluid sample stream to guide the fluid sample stream through the analysis region.

13. An X-ray apparatus according to claim 12 wherein the fluid sample stream has a density of between 1% and 70% of the density of the individual particles.

14. An X-ray apparatus according to claim 12 wherein the sample nozzle is shaped to have a flat inner cavity and a slit exit, the width of the slit exit being narrower than the flat inner cavity, the outside of the sample nozzle tapering at the exit to direct the fluid sample stream between the source and detector.

15. An X-ray apparatus according to claim 12 wherein the sample nozzle is shaped to generate the fluid sample stream in the form of a flat sheet having a thickness of less than 2mm and a width of at least 5mm.

16. An X-ray apparatus according to claim 12 further comprising protective plates between the analysis region and the source and between the analysis region and the detector, the protective plates being transparent to X-rays and spaced from the analysis region so that the plates are spaced from the fluid sample stream in use.

17. An X-ray apparatus according to claim 12 wherein the X-ray source is on one side of the analysis region arranged to transmit X-rays through the analysis region to the detector for carrying out X-ray analysis as a transmission arrangement.

18. An X-ray apparatus according claim 17 further comprising an X-ray mirror between the X-ray source and the detector for focusing the X-rays through the analysis region towards the detector.

19. An X-ray apparatus according to claim 14, wherein the fluid stream is a gas stream.

* * * * *

UNITED STATES PATENT AND TRADEMARK OFFICE
CERTIFICATE OF CORRECTION

PATENT NO. : 7,477,724 B2
APPLICATION NO. : 11/377908
DATED : January 13, 2009
INVENTOR(S) : Roger Meier et al.

It is certified that error appears in the above-identified patent and that said Letters Patent is hereby corrected as shown below:

In Col. 6, line 42
replace "gas fluid sample"
with "gas sample"

In Col. 6, line 48
replace "gas fluid sample"
with "gas sample"

In Col. 7, line 17
replace "gas fluid sample"
with "gas sample"

In Col. 7, line 18
replace "gas fl-ttiA stream"
with "gas stream"

In Col. 7, line 19
replace "gas fl-tti-d sample"
with "gas sample"

Signed and Sealed this

Sixteenth Day of June, 2009

JOHN DOLL
*Acting Director of the United States Patent and Trademark Office*